United States Patent [19]
Volgyesi

[11] Patent Number: 5,134,284
[45] Date of Patent: Jul. 28, 1992

[54] METHOD OF TESTING THE ACCURACY OF PULSE OXIMETERS AND DEVICE THEREFOR

[76] Inventor: George A. Volgyesi, 36 Gatehead Road, Willowdale, Ontario, Canada, M2J 2P5

[21] Appl. No.: 691,412

[22] Filed: Apr. 25, 1991

[51] Int. Cl.$^5$ ............................................. G01D 18/00
[52] U.S. Cl. ................................................. 250/252.1
[58] Field of Search ..................... 250/252.1 A, 343; 356/41, 42; 128/633

[56] References Cited

U.S. PATENT DOCUMENTS

| | | | |
|---|---|---|---|
| 4,621,643 | 11/1986 | New, Jr. et al. | 250/252.1 X |
| 4,834,532 | 5/1989 | Yount | 250/252.1 X |
| 4,968,137 | 11/1990 | Yount | 250/252.1 X |

OTHER PUBLICATIONS

Merrick et al., "Continuous, Non-Invasive Measurements of Arterial Blood Oxygen Levers", Hewlett-Packard Journal, vol. 28, No. 2, pp. 2–6, 1976.
De Kock, J. P. and Tarassenko, L., J. Biomed Eng., 13 (Jan.): 61–66, 1991.
A. J. Munley et al., The Lancet, May 13, 1989.
Y. Mendelson et al., IEEE Transactions on Biomedical Engineering, 13, No. 6, Jun. 1989.
Canadian Journal of Anaesthesia 37(4), 567, 1990.
Anesthesiology 73(3A), A427, 1990.
Canadian Journal of Anaesthesia 37(4), 588, 1990.

Primary Examiner—Constantine Hannaher
Assistant Examiner—Edward J. Glick
Attorney, Agent, or Firm—Riches, McKenzie & Herbert

[57] ABSTRACT

Device and method for testing the accuracy of pulse oximeters used in estimating arterial blood saturation levels. The device is for use in enabling a pulse oximeter to measure the absorption of the radiation emitted by the oximeter by a pulsatile liquid contained within the device, which device comprises the liquid, a resiliently flexible displaceable member adjacent the liquid which in operation is made to rhythmically move with a steady frequency and amplitude so as to effect a change in the depth of a volume of liquid in the direction acted upon by the radiation such that the liquid is operably provided in pulsatile form while under the influence of the radiation. The device provides a cheap and convenient method of testing the accuracy of the pulse oximeters.

8 Claims, 2 Drawing Sheets

METHOD OF TESTING THE ACCURACY OF PULSE OXIMETERS AND DEVICE THEREFOR

FIELD OF THE INVENTION

This invention relates to pulse oximeters used to measure blood oxygen saturation levels and more particularly to a method of checking the accuracy of such pulse oximeters and a device therefor.

BACKGROUND OF THE INVENTION

Pulse oximeters have become one of the most useful clinical monitors in the modern practice of anaesthesia in providing a convenient estimation of arterial blood oxygen saturation.

Typically, in operation a sensor containing light sources is attached to a patient's finger or ear lobe and the absorbency of the radiation passing through the tissue is measured. The pulse oximeter solves an equation that involves the pulsatile component of the differential absorption of specific red, typically 660 nm wavelength and infrared, typically, 930 nm wavelength, by transilluminated tissue.

For general background see Anesthesiology, 1983, 59, No 4, Oct 349-352, EVALUATION OF PULSE OXIMETRY Yelderman et al; Anaesthesia, 1988, 43, 229-232, THE ACCURACY OF PULSE OXIMETERS Taylor et al; Biomedical Technology Today, Nov./Dec. 1988, 210-214, ASSESSING PATIENT OXYGENATION R.P. Smith; and Anesth. Analg 1989, 68, 368-76, PRINCIPALS OF PULSE OXIMETRY: THEORETICAL AND PRACTICAL CONSIDERATIONS Alexander et al; D. Tobler, Discussion IX in Payne J.P., Severing Haus J.W. (Editors) "Pulse Oximetry" NY. Springer Verlag 1986, p.185-93.

Thus the pulse oximeter has become a vital tool of non-invasive patient monitoring in enabling the oxygen saturation level of blood to be measured.

Important clinical decisions are frequently made based entirely on blood oxygen saturation measurements obtained by pulse oximetry. However, due to the fact that the pulse oximeter requires the presence of pulsatile blood for its operation it is difficult to quickly, inexpensively and conveniently assess the functioning and accuracy of the oximeter. It is also unfortunate that pulse oximeters cannot be easily calibrated by the user since it relies on built-in calibration curves for its accuracy.

Mendelson et al., IEEE Transactions on Biomedical Engineering, 1989; 36, 625-27, AN IN VITRO TISSUE MODEL FOR EVALUATING THE EFFECT OF CARBOXYHEMOGLOBIN CONCENTRATION ON PULSE OXIMETRY describes an in vitro method for calibrating a pulse oximeter, which method is rather cumbersome, expensive and requires large quantities of blood. Munley et al, The Lancet, May 13, 1989, 1048-49, A TEST OBJECT FOR ASSESSING PULSE OXIMETERS, describe a test object for assessing pulse oximeters using a test object consisting essentially of a dummy "finger" with a rotating cone. However, this suffers from disadvantages overcome by the present invention.

The device of Munley et al requires a test object which is difficult, time consuming and expensive to construct It requires two hands of an operator and must be perfectly positioned relative to the sensor for accurate operation. The test object cannot be used to estimate the oxygen saturation level of blood nor to test the potential errors introduced by various physiological variables, such as hemoglobin concentration or skin pigmentation, in determining accuracy of pulse oximeters.

In contrast, the test device of the present invention is easy, fast and inexpensive to construct. The sensor need not be perfectly positioned on the test device for an accurate determination. Further, the latter is operated using only one hand of an operator and can be used to estimate the oxygen saturation of blood and to readily estimate the effect of physiological variables on the accuracy of pulse oximeters. Yet further, the amplitude of the signal produced by the device o the present application is controllable by the operator, whereas that of the Munley et al device is dependent on the amplitude of the pulsatile signal produced and fixed by the geometry of the Munley device, which may be too high or too low for some pulse oximeters.

It is an object of the present invention to provide a method of testing the accuracy of pulse oximeters which is quick, inexpensive and convenient.

It is a further object of the present invention to provide a device for use with a pulse oximeter to easily check said oximeter.

SUMMARY OF THE INVENTION

Accordingly, the invention provides in its broadest aspect a device for use in enabling a pulse oximeter to measure the absorption of the radiation emitted by said oximeter by a pulsatile liquid contained within said device, which device comprises said liquid, a resiliently flexible displaceable member adjacent said liquid and means for operably effecting rhythmic movement of said displaceable member with a steady frequency and amplitude so as to effect a change in the depth of a volume of said liquid in the direction acted upon by said radiation such that said liquid is operably provided in pulsatile form while under the influence of said radiation.

By the term "pulsatile liquid" is meant a volume of liquid whose depth through which the oximeter radiation is directed changes in a rhythmical manner with a steady frequency and amplitude. Thus, the depth or thickness of the liquid through which the radiation acts upon i.e. passes through in a, typically, lateral direction, varies in the regular manner as required by the oximeter In a preferred embodiment the invention provides a device as hereinbefore defined further comprising a rigid member, which with said displaceable member defines said volume operably occupied by said liquid, and wherein said means for operably effecting said rhythmic movement of said displaceable member effects said movement relative to said rigid member so as to effect said change in the depth of said volume of said liquid.

It will be appreciated, that the displaceable member and rigid member must be essentially non-absorbent, i.e. transparent, to the infrared and red light radiation emitted and subsequently measured by the pulse oximeter.

Thus, a preferred embodiment may take the form of a device having a pair of hollow, coaxially disposed concentric thermoplastic tubes, one within the other, and having a thin layer of liquid between them. The outer tube is rigid while the inner tube is wholly compliant or comprises a resiliently flexible portion. The liquid between the tubes acts as a compound filter to the infrared and red light radiation; the depth of which liquid can be modulated to a pulsatile form by applying pressure to a compliant squeeze-bulb connected to the inside tube.

In an alternative preferred embodiment, the liquid is contained in a single thermoplastic tube comprising the displaceable member, wherein the pulsatile effect is created in the liquid by the rhythmic displacement of the tube side walls, constituting displaceable members, one wall relative to the other.

The rhythmic pulsatile action of the liquid by the movement of the displaceable member is preferably effected by the deformation action of a squeeze bulb, typically of a spherical or bellow-like form, which cooperates with the displaceable member by means of a fluid, such as air or water.

When the squeeze bulb is compressed, the compressed fluid flexes the displaceable member to effect a reduction in the depth of the liquid filter This compression act is repeated, typically, 100-150 times per minute to create the pulsatile effect in the liquid.

The liquid filter used in the device comprises an aqueous solution of various proportions of a compound, for example, cupric chloride or cupric sulphate, which absorbs infrared radiation, and a solution which absorbs red light, such as blue ink. The relative amount of blue ink in admixture with the copper salt solution determines the degree of absorption of the visible red and infrared wavelengths, 660 and 940 mm, respectively, used with standard pulse oximeters. Clearly, pulse oximeters using radiation of alternative wavelengths would require radiation absorbing solutions appropriate to those specific alternative wavelengths. Thus, the specific liquids of the device constitute standard solutions equating to known saturation values and, accordingly, can provide a check on the accuracy of the pulse oximeter The range of saturation standards possible using the above liquid compositions covers the spectrum of from 0 to 100% saturation value.

To perform an accuracy check on a pulse oximeter, its' sensor is placed around the device and pulsations are induced by squeezing the bulb rhythmically with a steady frequency and amplitude until a stable reading is obtained on the pulse oximeter. This reading is then compared to the "true" value provided with the device. This procedure may then be repeated with several devices calibrated to different standard saturation values.

The calibrating standard solutions are preferably hermetically sealed within the device.

In a further aspect, the invention provides a method of testing the accuracy of a pulse oximeter which method comprises using a device according to the invention as hereinbefore defined.

Thus, the invention advantageously provides a device for testing the accuracy of a pulse oximeter, which device requires only a single specific and standard radiation absorbing solution, which may be used with different sensor types which need not be perfectly positioned for accuracy; which is adapted to provide a signal amplitude determined by an operator; which can be used to measure the oxygen saturation of blood; and for the purpose of research to estimate the effect of physiological variables on the accuracy of pulse oximeters, for instance, the effect of skin pigmentation or hemoglobin content on the pulse oximeter reading.

Accordingly, the invention provides a device as hereinbefore defined which is easily and conveniently operable by the fingers or one hand of an operator.

DESCRIPTION OF THE PREFERRED EMBODIMENTS

In order that the invention may be better understood, preferred embodiments will now be described by way of example only with reference to the accompanying drawings wherein.

Figure 1:
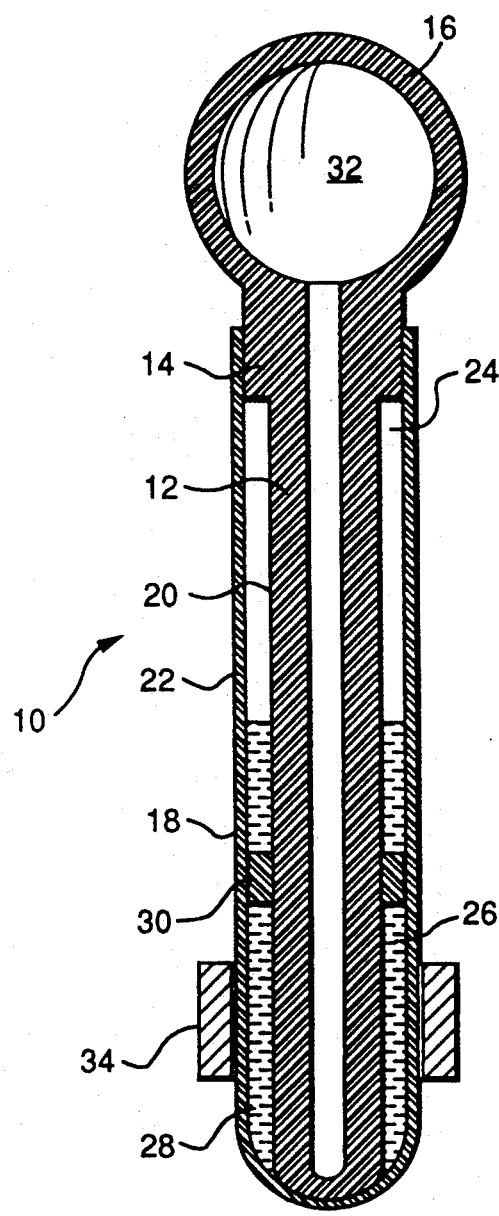
FIG. 1 is a diagrammatic sketch of a vertical section of a manually operable device according to the invention for use with a pulse oximeter (only the sensor of which is shown)

The device shown generally as a finger-shaped model 10 in FIG. 1 comprises a hollow air-filled tube 12 formed of resiliently flexible SILASTIC TM thermoplastic material (Dupont, U.S.A.) having an integrally formed shoulder 14 and squeeze bulb 16. Tube 12 is held within a tube 18, formed of a rigid thermoplastic material, by means of shoulder 14. Tubes 12 and 18 have walls 20 and 22, respectively, which define an annular space 24 which at a lower part contains a volume 26 (1 ml.) of an aqueous solution 28 of cupric chloride and blue ink dye. The cupric chloride partially absorbs infrared radiation (940 nm) and methylene blue ink dye partially absorbs the visible red radiation (660 nm). The aqueous solution has a known "blood oxygen saturation" value associated, therewith, determined by a known, factory accurate pulse oximeter.

An annular spacer 30 is provided between tubes 12 and 18 to maintain concentricity of said tubes. Squeeze bulb 16 contains a fluid 32.

Tube 18 is adapted by means (not shown) to fit between pulse oximeter sensor 34 of a pulse oximeter (not shown.)

In operation, to check the accuracy of a pulse oximeter the following procedure is followed.

Device 10 is inserted between the pulse oximeter sensor 34 wherein infrared and red light radiation emitted from the pulse oximeter acts upon or influences a depth of liquid 28, in a lateral direction in the embodiment shown. Pulsations in the liquid are produced by finger squeezing bulb 16, manually 100 to 150 times a minute in a rhythmic manner to provide a steady frequency and amplitude to the movement of the displaceable member 12. The blood oxygen saturation value for the pulsatile liquid 28 as read from the pulse oximeter is compared to that associated with the standard liquid 28.

Figure 2:
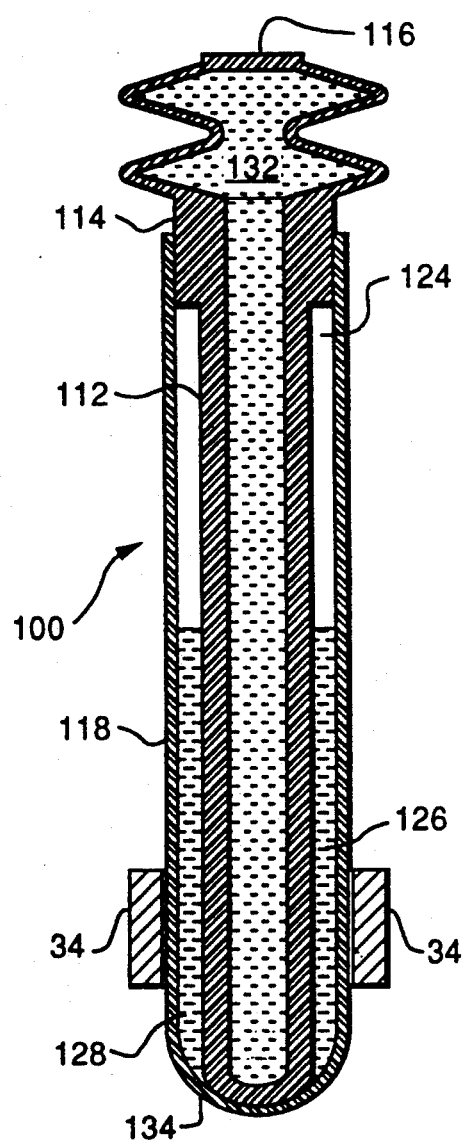
FIG. 2 is a diagrammatic sketch of a vertical section of an alternative manually operable embodiment of a device according to the invention.

The embodiment shown in FIG. 2 comprises the device shown generally as 100 having an inner tube 112 filled with water 132 and a bellow-type squeeze bulb 116. Tube 112 is tightly held in an outer tube 118 by shoulders 114. The walls of tubes 112 and 118 define annular space 124 having cupric chloride-blue ink aqueous solution 128 at a lower portion 126 thereof. Tube 112, at its lower extremity 134 within tube 118, abuts tube 118 to provide a non-movable fit.

In operation, squeeze bulb 116 creates pulsatile liquid of the aqueous solution 128 by manual compression using merely a thumb of bulb 116 coaxially, inwardly, of tube 112.

Figures 3, 4:
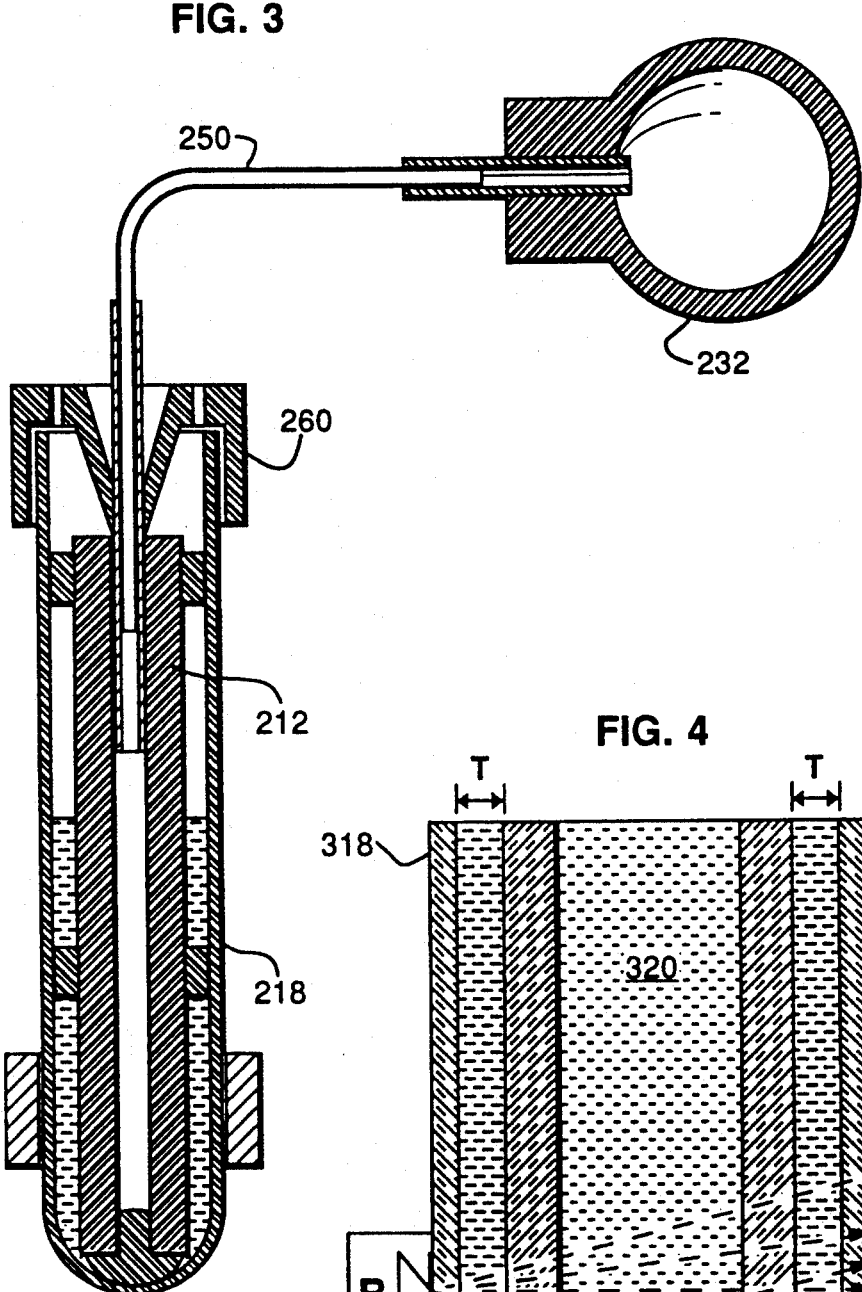
FIG. 3 is a diagrammatic sketch of a vertical section of another alternative embodiment of a device according to the invention.
FIG. 4 shows a schematic diagram of a vertical cross-section of a device according to the invention under the action of a pulse oximeter radiation source and photo detector sensor.

The alternative embodiment shown in FIG. 3 comprises an air-filled spherical bulb 232 cooperating by means of air-filled low compliance thermoplastic conduit 250 with an air-filled inner tube 212 rigidly held in an outer tube 218 by a thermoplastic cap 260. Tube 218 is operably held by a sensor of a pulse oximeter.

In operation, rhythmic compression of the fluid, air, in bulb 232 effects compression of the fluid, air, in conduit 250 and tube 212 to effect pulsatile movement of tube 212 and to produce pulsatile fluid.

FIG. 4 shows in schematic form a rigid member of an outer tube 318 and a resiliently flexible displaceable member of inner tube 312, which members together define a volume which is occupied by a liquid 328 having a thickness "T" modulated by pressure pulsations acting upon tube 312 by fluid 320 by squeeze-bulb means (not shown). The phantom lines indicate infrared and visible red radiation from the pulse oximeter influencing and acting upon the device.

Oximeter light source 330 provide simultaneous infrared and visible red radiation, the residue of which is picked up by photo detector 340 of a pulse oximeter sensor.

In an alternative, but less preferred embodiment, a variation of the device as shown in FIG. 3 has a squeeze bulb and conduit in communication with the enclosed annular space defined by the two tubes and wherein the liquid filter is contained within the inner tube.

Although this disclosure has described and illustrated certain preferred embodiments of the invention, it is to be understood that the invention is not restricted to these particular embodiments. Rather, the invention includes all embodiments which are functional or mechanical equivalents of the specific embodiments and features that have been described and illustrated herein.

What I claim is:

1. A device for use in enabling a pulse oximeter which provides radiation for action upon a pulsatile liquid to measure the absorption of the radiation emitted by said oximeter by a pulsatile liquid contained within said device, which deice comprises said liquid, a resiliently flexible displaceable member adjacent said liquid and manually operable to effect rhythmic movement of said displaceable member with a steady frequency and amplitude so as to effect a change in the depth of a volume of said liquid in the direction acted upon by said radiation such that said liquid is operably provided in pulsatile form while under the influence of said radition.

2. A device as claimed in claim 1 further comprising a rigid member, which with said displaceable member defines said volume operably occupied by said liquid, and wherein said manual operation of said displaceable member to effect said rhythmic movement of said displaceable member effects said movement relative to said rigid member so as to effect said change in the depth of said volume of said liquid.

3. A device as claimed in claim 1 comprising a hollow resiliently flexible tube as said displaceable member and containing said liquid.

4. A device as claimed in claim 2 comprising a hollow rigid tube as said rigid member; and
a hollow resiliently flexible tube as said displaceable member and disposed within said rigid tube to provide an intervening volume; and wherein said intervening volume comprises said volume of liquid.

5. A device as claimed in any one of claims 1 to 4 further comprising a fluid cooperable with a second resiliently flexible material such that deformation of said second resiliently flexible material effects compression of said fluid to effect displacement of said displaceable member when said manual operation of said displaceble member effects said rhythmic movement of said displaceable member.

6. A device as claimed in any one of claims 1 to 4 wherein said liquid is an aqueous solution of a compound which absorbs infrared radiation and a compound which absorbs visible red radiation.

7. A manually operable device for checking the accuracy of a pulse oximeter, which oximeter provides radiation for action upon a pulsatile liquid, which device comprises:
a rigid thermoplastic tube;
a resiliently flexible thermoplastic tube comprising a displaceable wall and disposed within said rigid tube to define an annular intervening space and which flexible tube contains a first fluid;
said thermoplastic tubes being essentially transparent to said radiation;
a fluid containing resiliently flexible squeeze bulb containing said first fluid;
said liquid comprising an aqueous solution of an infrared radiation absorbing compound and a visible red radiation absorbing compound, and contained within said intervening space to constitute a volume of said liquid; and wherein said flexible tube cooperates with said squeeze bulb such that an operable rhythmic compression with a steady frequency and amplitude of said squeeze bulb effects a rhythmic displacement of said displaceable wall relative to said rigid tue with a steady frequency and amplitude so as to effect a change in the depth of said volume of said liquid in the direction acted upon by said radiation such that said liquid is operably provided in pulsatile form while under the influence of said radiation.

8. A method of checking the accuracy of a pulse oximeter which oximeter provides radiation for action upon a plusatile liquid, which method comprises providing a standard liquid in pulsatile form for sue with said oximeter and obtaining a measurement with said oximeter, wherein said liquid is manually provided in pulsatile form by the action of a resiliently flexible member upon said liquid to effect rhythmical changes with a steady frequency and amplitude in the depth of a volume of said liquid in the direction acted upon by said radiation.

* * * * *